United States Patent [19]

Baus et al.

[11] Patent Number: 4,988,721
[45] Date of Patent: Jan. 29, 1991

[54] 0-(1,2,4-TRIAZOL-1-YL) O-PHENYL ACETALS USEFUL AS FUNGICIDES

[75] Inventors: Ulf Baus, Dossenheim; Wolfgang Reuther, Heidelberg; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 477,730

[22] Filed: Feb. 9, 1990

[30] Foreign Application Priority Data

Feb. 24, 1989 [DE] Fed. Rep. of Germany ....... 3905766

[51] Int. Cl.$^5$ .................. A01N 43/653; C07D 249/08
[52] U.S. Cl. ..................... 514/383; 514/184; 548/101; 548/262.2; 548/268.6
[58] Field of Search ................ 514/383, 184; 548/262.2, 268.6, 101

[56] References Cited

U.S. PATENT DOCUMENTS

| | | | |
|---|---|---|---|
| 3,952,002 | 4/1976 | Kramer et al. | 514/383 |
| 4,147,791 | 4/1979 | Meiser et al. | 514/383 |
| 4,618,619 | 10/1986 | Regel et al. | 514/383 |
| 4,740,516 | 4/1988 | Regel et al. | 514/383 |

FOREIGN PATENT DOCUMENTS

| | | | |
|---|---|---|---|
| 0002671 | 7/1979 | European Pat. Off. | |
| 1364619 | 8/1974 | United Kingdom | 514/383 |

OTHER PUBLICATIONS

Wazny et al., "The Reflectance method ", etc. Wood Sci. Technol. 23 pp. 179–189 (1989).
Morrell et al., "Fungi Colonizing Redwood etc.", Wood and Fiber Science, 20 (2) pp. 243–249 (1988).

Primary Examiner—Glennon H. Hollrah
Assistant Examiner—Patricia L. Morris
Attorney, Agent, or Firm—Oblon, Spivak, McClelland, Maier & Neustadt

[57] ABSTRACT

Compounds of the general formula

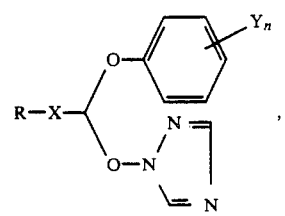

where
R is alkyl or substituted or unsubstituted aryl,
X is C=O or CHOH and derivatives thereof,
Y is hydrogen, alkyl, alkoxy, halogen, aryl or aryloxy, and
n is 1 to 5,
and fungicides containing these compounds.

5 Claims, No Drawings

O-(1,2,4-TRIAZOL-1-YL) O-PHENYL ACETALS USEFUL AS FUNGICIDES

The present invention relates to novel N-hydroxytriazole derivatives, the salts and metal complexes thereof, a process for the preparation thereof and the use thereof as fungicides.

It has been disclosed to use O-(N-triazolyl) acetals, e.g. 1-(4-chlorophenoxy)-3,3-dimethyl-1-(1,2,4-triazol-1-yl)-2-butanone (DE 2,201,063) or 1-(4-chlorophenoxy)-3,3-dimethyl-1-(1,2,4-triazol-1- yl)-2butanol, as fungicides (DE 2,324,010). However, their action is not always satisfactory.

We have now found that compounds of the general formula

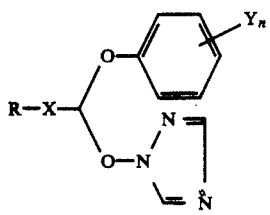

where
R is tert-alkyl of 4 to 6 carbons or aryl which may be substituted by halogen, phenyl, aryloxy or alkoxy,
X is C=O or CHOH and derivatives thereof,
Y is halogen, alkyl of 1 to 9 carbons, alkoxy, halogen, aryl or aryloxy and
n is 1 to 5 and the salts and metal complexes thereof have a surprisingly good fungicidal action.

R is, for example, tert-butyl, or aryl (phenyl) which can be substituted one to five times (up to three times) by halogen (Cl, Br, F), aryloxy (phenoxy) or $C_1$-$C_4$-alkoxy, (methoxy, ethoxy, tert-butoxy),
X is C=O or CHOH and derivatives thereof, e.g. ethers

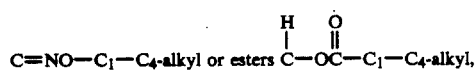

Y is, for example, $C_1$-$C_4$-alkyl (methyl, ethyl, tert-butyl), $C_1$-$C_4$-alkoxy (methoxy, ethoxy, tert-butoxy), halogen (Cl, Br, F), aryl (phenyl), aryloxy (phenoxy), e.g. 4-chloro or 3-methyl-4-chloro,
n is, for example, 1, 2, 3, 4 or 5, and when n is greater than 1 the Y radicals are identical or different.

Examples of salts are the acid addition salts which are tolerated by plants, e.g. salts with inorganic or organic acids, such as the salts of hydrochloric acid, hydrobromic acid, nitric acid, oxalic acid, acetic acid, sulfuric acid, phosphoric acid or dodecylbenzenesulfonic acid. The activity of the salts derives from the cation, so that the choice of the anion is arbitrary.

It is furthermore possible to convert the compounds of the formula I into metal complexes by conventional methods This can take place by reacting these compounds with metal salts, e.g. salts of copper, zinc, iron, manganese or nickel, for example copper(II) chloride, zinc(II) chloride, iron(III) chloride, copper(II) nitrate, manganese(II) chloride or nickel(II) bromide.

We have furthermore found that the compounds of the general formula I (X=C=O) can be prepared very easily and in good yields by reacting 1-hydroxy-1,2,4-triazole with the compounds of the general formula II,

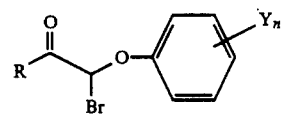

where
R, Y and n have the abovementioned meanings. The compounds of the general formula II are known or can be prepared by conventional processes (e.g. DE 2,201,063). 1-hydroxy-1,2,4-triazole is prepared as follows, for example:

103.5 g (1.5 mol) of 1H-1,2,4-triazole were dissolved in 1344 g (12 mol) of 50% strength aqueous potassium hydroxide. While cooling in ice, 340 g (3 mol) of 30% strength $H_2O_2$ and, a little at a time, 555 g (3.75 mol) of phthalic anhydride were added, and the mixture was stirred at 20° to 30° C. for 2 hours It was subsequently acidified to a pH below 1.5 with approx. 35% strength sulfuric acid, the resulting precipitate was filtered off with suction, and the filtrate was worked up in a conventional manner. 19 g of 1-hydroxy-1,2,4-triazole of melting point 132° C. were obtained. This is a yield of 15% of theory.

The reaction with the compound II is carried out, for example, in an inert organic solvent such as tetrahydrofuran (THF), dimethyl sulfoxide (DMSO), dimethylformamide (DMF) or diethyl ether, preferably THF or a THF/water mixture, in the presence of a base such as triethylamine, tributylamine, NaOH, sodium carbonate or pyridine, at from 0° to 100° C., preferably at room temperature (20° C.). The compounds of the general formula I (X=C=O) result as racemates which can be separated into their isomers in a conventional manner. The invention relates both to the pure enantiomers and to the mixtures thereof, all of which are suitable as fungicides.

We have furthermore found that the compounds of the general formula I (X=C=O) can be converted with conventional reducing agents such as $NaBH_4$, lithium aluminum hydride (LAH) or $NaCNBH_3$ into the compounds of the general formula I (X=CHOH). The compounds of the general formula I (X=CHOH) result as racemic diastereomer mixtures which can be separated into their isomers in a convention manner. The invention relates both to the pure isomers and to the mixtures thereof, all of which are suitable as fungicides.

Derivatives are obtained from the compounds in which X is C=O in a conventional manner, e.g. the oximes which X is C=NOH by reaction with hydroxylamine, or the oxime ethers in which X is C=NO—$C_1$-$C_4$-alkyl by reaction with O—$C_1$-$C_4$-alkylhydroxylamine.

Derivatives are obtained from the compounds in which X is CHOH in a conventional manner, e.g. the esters in which X is

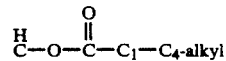

by reaction with carboxylic acids $C_1$-$C_4$—COOH.
The ethers in which X is

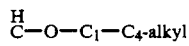

are obtained by reaction with $C_1$–$C_4$-alkyl halides.

PREPARATION EXAMPLES

EXAMPLE 1

1.7 g (20 mmol) of 1-hydroxy-1,2,4-triazole are dissolved in 75 ml of THF. While stirring, 6.1 g (20 mmol) of 1-bromo-1-(4-chlorophenoxy)-3,3-dimethyl-2-butanone and then 2 g (20 mmol) of triethylamine are added. After 2 hours, the resulting precipitate is filtered off with suction. The filtrate is concentrated, the residue is taken up in ethyl acetate/ether (1:1), and the solution is washed with water and dried. Removal of the solvent results in 6.2 g (100% of theory) of compound No. 1 in the form of an oily crude product which is crystallized from cyclohexane. Melting point: 82° C.

| | |
|---|---|
| Melting point: 82° C. | |
| Analysis: $C_{14}H_{16}ClN_3O_3$ | calc.: C 54.3 H 5.2 N 13.5 |
| (309.61) | found: C 54.3 H 5.4 N 13.4 |
| H NMR (CDCl$_3$): | 1.27 (s, 9H); 6.35 (s, 1H); |
| | 6.97–7.37 (m, 4H); 7.78 (s, 1H); |
| | 8.1 (s, 1H) [ppm]. |

The following were obtained in a corresponding manner:

| No. | R | X | Y | Phys. data |
|---|---|---|---|---|
| 1 | C(CH$_3$)$_3$ | C=O | 4-Cl | m.p.: 82° C. |
| 3 | C(CH$_3$)$_3$ | C=O | 2,4-Cl$_2$ | m.p.: 62–64° C. |
| | | | | H NMR: 1.28 (s, 9H); 6.32 (s, 1H); 7.08–7.43 (m, 3H); 7.78 (s, 1H); 8.18 (s, 1H). |

EXAMPLE 2

Reduction of compound No 1 to alcohol No 2:

4.64 g (15 mmol) of 1-(4-chlorophenoxy)-1-(1,2,4-triazol-1-yloxy)-3,3-dimethyl-2-butanone (compound No. 1) are dissolved in 100 ml of THF/MeOH (1:1). Then, while stirring, 0.57 g (15 mmol) of NaBH is added. After 1 hour, the mixture is poured into water, made slightly acid and extracted with ethyl acetate. The organic phase is washed with water and dried. Removal of the solvent results in 4.64 g (99% of theory) of a viscous oil (compound No. 2).

| | |
|---|---|
| H NMR (CDCl$_3$): | 0.99 and 1.03 (2s, 9H); 3.33 and 3.75 (2d, 1H; 5.69 and 5.99 (2d, 2H); 6.8 (m, 4H); 7.74, 7.78, 7.82 and 8.02 (4s, 2H). |

The following were obtained in a corresponding manner:

| No. | R | X | Y | Phys. data | |
|---|---|---|---|---|---|
| 2 | C(CH$_3$)$_3$ | CHOH | 4-Cl | See Example 2 | |
| 4 | C(CH$_3$)$_3$ | CHOH | 2,4-Cl$_2$ | H NMR (CDCl$_3$): | 1.03 and 1.08 (2s, 9H); 3.36 and 3.47 (2d, 1H); 5.83 and 6.03 (2d, 1H); 6.7–7.45 (m, 3H); 7.73, 7.8, 7.82 and 8.08 (4s, 2H). |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Pucciinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants if water is used as solvent, it is also possible to employ other organic solvents as auxiliary solvents. Suitable auxiliaries for this purpose are solvents such as aromatics e.g., xylene, chlorinated aromatics (e.g., chlorobenzenes. paraffins e.g., crude oil fractions, alcohols e.g., methanol, butanol, ketones e.g., cyclohexanone), amines (e.g., ethanolamine, dimethylformamide, and water; carriers such as ground natural minerals (e.g., kaolins, aluminas, talc and chalk) and ground synthetic minerals (e.g. highly disperse silica and silicates); emulsifiers such as nonionic and anionic emulsifiers e.g., polyoxyethylene fatty alcohol ethers, alkyl sulfonates and aryl sulfonates; and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii.*

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 (Table 1) is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 4 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 4 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts by weight of the sodium salt of a phenolsulfonic acid-ureaformaldehyde condensate. 2 parts of silica gel and 48 parts of water to give a stable aqueous dispersion. Dilution in water gives an aqueous dispersion.

IX. 20 parts by weight of compound no. 4 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLE 1

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity 90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 1, 2 and 4, applied as 0.0125 wt % spray liquors, have a good fungicidal action (100%).

We claim:

1. A compound of the formula (I):

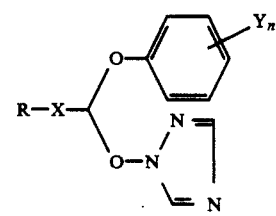

wherein

R is tert-alkyl of from 4 to 6 carbons, phenyl or phenyl which is substituted form 1 to 5 times by halogen, phenyl, phenoxy or alkoxy of from 1 to 4 carbons, X is C=O, C=NOH, C=NOR', CHOH, CHOR', or CHOC(=O)R', wherein R' is alkyl of from 1 to 4 carbons, Y is hydrogen, alkyl of from 1 to 9 carbons, alkoxy of from 1 to 4 carbons, halogen, phenyl, or phenoxy, n is from 1 to 5;

acid addition salts thereof, wherein said acid is selected from the group consisting of hydrochloric, hydrobromic, nitric, oxalic, acetic, sulfuric, phosphoric, and dodecylbenzenesulfonic acid, and metal complexes thereof, wherein said metal is selected from the group consisting of cooper, zinc, iron manganese and nickel.

2. A fungicidal composition containing a fungicidally acceptable carrier and a fungicidally effective amount of a compound of the formula (I):

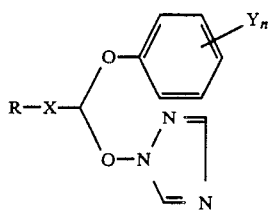

wherein:
R is tert-alkyl of from 4 to 6 carbons, phenyl of phenyl which is substituted from 1 to 5 times by halogen, phenyl, phenoxy or alkoxy of from 1 to 4 carbons,
X is C=O, C=NOH, C=NOR', CHOH, CHOR', or CHOC(=O)R', wherein R' is alkyl of from 1 to 4 carbons,
Y is hydrogen, alkyl of from 1 to 9 carbons, alkoxy of from 1 to 4 carbons, halogen, phenyl, or phenoxy,
n is from 1 to 5, and
a fungicidally acceptable salt or metal complex thereof.

3. A process for combating fungi, wherein the fungi, or the plants, seed, or wood threatened by fungus attack are treated with a fungicidal composition containing a fungicidally effective amount of a compound of the formula (I):

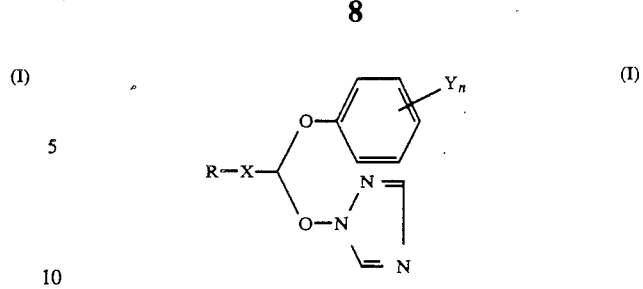

wherein:
R is tert-alkyl of from 4 to 6 carbons, phenyl of phenyl which is substituted from 1 to 5 times by halogen, phenyl, phenoxy or alkoxy of from 1 to 4 carbons,
X is C=O, C=NOH, C=NOR', CHOH, CHOR', or CHOC(=O)R', wherein R' is alkyl of from 1 to 4 carbons,
Y is hydrogen, alkyl of from 1 to 9 carbons, alkoxy of from 1 to 4 carbons, halogen, phenyl, of phenoxy,
n is from 1 to 5, and
a fungicidally acceptable salt or metal complex thereof.

4. A compound as claimed in claim 1, wherein R is tert-butyl, X is C=O and $Y_n$ is 4-chloro or 2,4-dichloro.

5. A compound as claimed in claim 1, wherein R is tert-butyl, X is CHOH any $Y_n$ is 4-chloro or 2,4-dichloro.

* * * * *